United States Patent [19]

Zasloff

[11] Patent Number: 5,643,876
[45] Date of Patent: *Jul. 1, 1997

[54] BIOLOGICALLY ACTIVE SYNTHETIC MAGAININ PEPTIDES

[75] Inventor: Michael A. Zasloff, Rockville, Md.

[73] Assignee: The United States of America as represented by the Department of Health and Human Services, Rockville, Md.

[*] Notice: The term of this patent shall not extend beyond the expiration date of Pat. No. 4,810,777.

[21] Appl. No.: 963,007

[22] Filed: Oct. 19, 1992

Related U.S. Application Data

[63] Continuation of Ser. No. 507,263, Apr. 12, 1990, abandoned, which is a continuation of Ser. No. 76,734, Jul. 23, 1987, abandoned, which is a continuation-in-part of Ser. No. 21,493, Mar. 4, 1987, Pat. No. 4,810,777.

[51] Int. Cl.$^6$ .................... A61K 38/10; A61K 38/16; C07K 7/08; C07K 14/00
[52] U.S. Cl. .................... 514/13; 514/12; 514/2; 530/326; 530/325; 530/300; 530/800; 930/190; 930/10; 930/DIG. 811; 930/DIG. 821
[58] Field of Search .................... 514/13, 12, 2; 530/326, 325, 300, 800; 930/190, 10, DIG. 811, DIG. 821

[56] References Cited

U.S. PATENT DOCUMENTS

| | | | |
|---|---|---|---|
| 3,883,499 | 5/1975 | Tachibana et al. | 530/326 |
| 3,928,306 | 12/1975 | Uchiyama et al. | 530/326 |
| 4,962,277 | 10/1990 | Cuervo et al. | 514/14 |

OTHER PUBLICATIONS

Giovannini et al, *Biochem. J.*, 243:113–120, 1987.
Csordas et al, *Toxicon* & 103–108, 1969.
Eisenberg, Ann Rev. Biochem. 53:595–623, 1984.
Kaiser et al, *Proc. Natl. Acad. Sci. USA* 80:1137–1143, 1983.
Sures et al, Proc. Natl. Acad. Sco. USA 81:380–384, 1984.
*CRC Handbook of Chemotherapeutic Agents*, vol. I pp. 178–185. "Peptide Antibiotics".
Kempf et al, *J. Biol. Chem.* 257:2469–2476, 1982.
Steiner et al, *Nature* 292:246–248, 1981.
Hoffmann et al, Embo, J. 2:711–714, 1983.
Andreu et al, *Biochem.* 149:531–535, 1985.
Merrifield et al, *Biochem.* 21:5020–5031, 1982.
Gibson et al, *J. Biol Chem.* 261:5341–5349, 1986.
Richter et al, *Peptides* 6:17–21, 1985.
Hoffmann et al, The EMBO Journal, vol. 2, pp. 111–114, 1983.
Richter et al, The EMBO Journal, vol. 3, pp. 617–662, 1984.
Wakabayashi et al, Nucleic Acid Research, vol. 3, pp. 1817–1829, 1985.
Csordas et al, Monatshefte fur Chemie, vol. 101, pp. 182–189, (1970).
Chen et al, FEBS, vol. 236, pp. 462–446, 1988.
Richter et al, The Journal of Biological Chemistry, vol. 261 pp. 3676–3680, 1986.
Terwilliger et al, The Journal of Biological Chemistry, vol. 257, 1982, pp. 6016–6022.
The Merck Manual of Diagnosis and Therapy, 11th ed., pp. 761–778, (1966).

*Primary Examiner*—Ponnathapura Achutamurthy
*Assistant Examiner*—T. D. Wessendorf
*Attorney, Agent, or Firm*—Elliot M. Olstein; Raymond J. Lillie

[57] ABSTRACT

A class of broad spectrum bioactive polypeptides termed "Magainin" have been described. These peptides have a molecular weight of about 2500 or less, are highly water soluble, amphiphilic and non-hemolytic.

18 Claims, No Drawings

BIOLOGICALLY ACTIVE SYNTHETIC MAGAININ PEPTIDES

This application is a continuation of application Ser. No. 07/507,263, filed Apr. 12, 1990, now abandoned which application is a continuation of application Ser. No. 07/076,734, filed Jul. 23, 1987, abandoned, which is a Continuation In Part of application Ser. No. 07/021,493 filed with the U.S. Patent and Trademark Office on Mar. 4, 1987 now U.S. Pat. No. 4,810,777.

BACKGROUND OF THE INVENTION

The present invention relates generally to bioactive compounds. More particularly, the present invention is related to a new class of synthetic polypeptides, designated herein "Magainins", which have a broad range of bioactive properties. It is noted that the "Magainin" family of compounds having the properties as described herein have never heretofore been discovered or known.

SUMMARY OF THE INVENTION

It is, therefore, an object of the present invention to provide a novel family of synthetic compounds, termed "Magainins."

It is a further object of the present invention to provide a novel class of antimicrobial compounds capable of inhibiting the growth or proliferation of such organisms as gram-positive and gram-negative bacteria, fungi, virus, protozoan species and the like.

Various other objects and advantages will become apparent from the Detailed Description of the Invention.

DETAILED DESCRIPTION OF THE INVENTION

The above and various other objects and advantages of the present invention are achieved by Magainins which are defined as a class of substantially pure, homogeneous polypeptides composed exclusively of about 25 amino acids, having a molecular weight of about 2500 or less, being water soluble at a concentration of greater than 5 mg per ml at neutral pH or in an aqueous solution of physiologic ionic strength, being amphiphilic, surface-seeking and having a broad spectrum of properties at physiologic ionic strength and pH. The Magainins are distinguishable from all other peptides reported in the literature at least with respect to their amino acid sequence. By computer search no analogous peptide with significant homology was found in the NIH protein and nucleic acid Data Banks (GenBank, 1986 Edition). Furthermore, the Magainins cannot be generated through simple substitutions of peptides of other classes with similar properties, such as cecropin, xenopsin, bombesin, mellitin and the like. Hence, Magainins represent a unique family of chemical substances, clearly defined at least in part by their unique amino acid sequence.

Table I shows the amino acid sequence (single letter code) of certain Magainin polypeptides of the present invention.

TABLE I

Primary Sequence of Magainin Polypeptides

Magainin I: $(NH_2)$GIGKFLHSAGKFGKAFVGEIMKS(OH)

Magainin II: $(NH_2)$GIGKFLHSAKKFGKAFVGEIMNS(OH)

Magainin III: $(NH_2)$GIGKFLHSAKKFGKAFVGEIMN(OH)

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

The term "bioactive" as used herein means having biological effect such as illustrated herein infra.

The term "antibiotic" as used herein means that the polypeptides of the present invention produce effects adverse to the normal biological functions of the cell, tissue or organism including death or destruction and prevention of the growth or proliferation of the biological system.

The term "antimicrobial" as used herein means that the polypeptides of the present invention inhibit, prevent or destroy the growth or proliferation of microbes such as bacteria, fungi, virus and the like.

The term "substantially pure" as used herein means as pure as it is possible to obtain by using the methods known to one of ordinary skill in the art.

Of course, having described the amino acid sequence of the Magainins, these polypeptides can be routinely synthesized in substantially pure form by standard techniques well known in the art, such as by commercially available peptide synthesizers and the like. Such standard techniques of polypeptide synthesis can be found described in such publications as Merrifield, J. Chem. Soc. 85: 2149–2154, 1963; Hunkapillar et al, Nature 310: 105–111, 1984.

It is noted, however, that the amino acid sequences of Magainins listed in Table I show only essential portions required for antibiotic activity. In otherwords, the polypeptides are not limited to the sequences shown in Table I, but must have, at least in part or in whole the amino acid sequence shown in Tables I and II. Of course, various analogs and derivatives of Magainins can be easily predicted, generated and/or prepared by such standard and common methods as NMR (nuclear magnetic resonance), computer modeling and the like and all such analogs or derivatives which are equivalent in structure and function to the Magainins as defined herein are encompassed within the scope of the disclosure contained herein. Some derivatives of Magainin II and their antimicrobial activities, for instance, are shown in Table II. It is clear from the results presented in Table II that the Magainins could be manipulated in various ways, for example, adding a carboxyl-terminal amide, progressively made shorter at the amino terminus, substituted with different amino acid residues at different positions of the molecule and the like so long as they retain or augment antimicrobial potency and/or other biological properties.

Table III shows the antimicrobial spectrum of the synthetic Magainin peptides of the present invention.

TABLE II

Antimicrobial Activity of Truncated Synthetic Derivatives of Magainin II

| Derivative | (Single Letter Code) | Zone of Inhibition on Lawn of *E. coli* Y1088 Generated by 50 μg of the Peptide (mm) |
|---|---|---|
| Magainin II(a) | (NH$_2$)IGKFLHSAKKFGKAFVGEIMNS(OH) | 10 |
| Magainin II(b) | (NH$_2$)GKFLHSAKKFGKAFVGEIMNS(OH) | 10 |
| Magainin II(c) | (NH$_2$)KFLHSAKKFGKAFVGEIMNS(OH) | 10 |
| Magainin II(d) | (NH$_2$)FLHSAKKFGKAFVGEIMNS(OH) | 2 |
| Magainin II(e) | (NH$_2$)LHSAKKFGKAFVGEIMNS(OH) | 1 |
| Magainin II(f) | (NH$_2$)HSAKKFGKAFVGEIMNS(OH) | 0 |
| Magainin II(g) | (NH$_2$)GIGKFLHSAKKFGKAFVGEIMNS(NH$_2$) | 15 |
| Magainin II(h) | (NH$_2$)GIGKYLHSAKKFGKAFVGEIMNS(NH$_2$) | 7 |

TABLE III

Antimicrobial Spectrum of Synthetic Magainin Peptides

| Organism (ATCC) | Magainin I | Magainin II | Magainin III |
|---|---|---|---|
| | Minimal Inhibitory Concentration (μg/ml) | | |
| *Eschericia coli* D31 | 1–20 | 1–10 | 1–10 |
| *Acinetobacter caloaceticus* (19606) | 7–35 | 1–7 | 7–35 |
| *Shigella sonnei* (25931) | 7–35 | 1–7 | 7–35 |
| *Enterobacter sonnei* (23355) | 7–35 | 1–7 | 7–35 |
| *Eschericia coli* (25922) | 7–35 | 1–7 | 7–35 |
| *Streptococcus pyogenes* (19615) | 7–35 | 1–7 | 7–35 |
| *Shigella flexneri* (12022) | 35–70 | 7–35 | 7–35 |
| *Citrobacter freundii* (8090) | >100 | 7–35 | 7–35 |
| *Enterobacter aerogenes* (13048) | >100 | 7–35 | >100 |
| *Klebisiella pneumonia* (13883) | >100 | 7–35 | >100 |
| *Staphyloccus epidermidis* (1228) | >100 | 7–35 | 35–70 |
| *Streptococcus faecalis* (19433) | >100 | 35–70 | >100 |
| *Pseudomonas aeruginosa* (27853) | >100 | 35–70 | 35–70 |
| *Salmonella typhimurium* (14028) | >100 | 35–70 | 35–70 |
| *Staphylococcus aureus* (25923) | >100 | 35–70 | >100 |
| *Candida albicans* (14053) | >100 | 35–70 | >100 |
| *Proteus vulgaris* (13315) | >100 | >100 | >100 |
| *Serratia marcescens* (8100) | >100 | >100 | >100 |

Table III also lists the range of minimal inhibitory concentrations for various organisms assayed in trypticase soy broth. These determinations were made following standard techniques well known in the art and described in such publications as, DIFCO Manual, 10th edition, 1984, pages 78–80.

Table IV lists the approximate concentration of Magainins which induces physical lysis of several representative protozoan species. These determinations were made by visual assessment of the treated organisms by light microscopy. Of course, the optimal effective antimicrobial concentration of a particular Magainin can be easily determined in a routine manner without undue experimentation by techniques well known to one of ordinary skill in the art.

It is pointed that the addition of a carboxyl-terminal amide to Magainin II results in about a 5-fold increase in potency of the peptide in several systems when compared to Magainin II. This increase in activity can be seen against bacteria, fungi, protozoa, and as shown in Table V, against tumor cells. This simple modification illustrates one of several ways of modifying the polypeptides of the present invention.

It is clear from the results presented herein supra that the Magainin polypeptides of the present invention have a broad range of potent biological activity including antimicrobial potency. Hence, it is apparent that the Magainins of the present invention allow a method of treating or controlling microbial infection caused by those organisms which are sensitive to Magainin. Such treatment comprises administering to a host or tissue susceptible to or afflicted with microbial infection an antimicrobial amount of Magainin.

Clearly, due to their antibiotic properties, the Magainins of the present invention can also be used as preservatives or sterilants of materials susceptible to microbial contamination.

TABLE IV

Antiprotozoan Activity of Synthetic Magainin Peptides

| Organism | Magainin I | Magainin II | Magainin III |
|---|---|---|---|
| | (Concentration required for osmotic lysis (μg/ml)) | | |
| *Paramecium caudatum* | 5 | 5 | 5 |
| *Amoeba proteus* | 5 | 5 | 5 |
| *Euglena gracilis* | 5 | 5 | 5 |

TABLE V

Comparison of Potencies of Magainin II and Magainin II(g)

| | MIC (μg/ml) | |
|---|---|---|
| Organism | Magainin II | Magainin II(g) |
| *E. coli* D-31 | 10 | 2 |
| *Pseudomonas aeruginosa* | 70 | 15 |

TABLE V-continued

Comparison of Potencies of Magainin II and Magainin II(g)

| | MIC (μg/ml) | |
|---|---|---|
| Organism | Magainin II | Magainin II(g) |
| Saccharomyces cerviscae | 50 | 10 |
| Acanthomeba castellani | 15 | 3 |

The substitution of phenylalanine at residue 5 by tyrosine results in a slight decrease in MIC of the derivative compared to Magainin II; however, a compensatory advantage of the tyrosine residue allows coupling of radioactive moieties such as 125 I and the like with the polypeptide molecule so that such radioactive derivatives can be employed in standard radio-immunoassay procedures to determine Magainin levels.

Anti-Protozoan Activity

Magainin II(g) has also been found to be active against the Malarial parasite, *Plasmodium gallinaceum*. Observations of activity were conducted by direct light microscopy. A sample of female and male zygotic forms of the chicken malarial parasite were suspended in phosphate buffered saline. Magainin II(g) was added to each at 100 ug/ml. Within seconds both forms underwent evident physical lysis. A control consisting of the addition of Magainin II(f) had no visible effect. The susceptibility of this strain of malaria suggests that the Magainins may be utilized as an anti-malarial agent in human Plasmodium infections.

It may be noted that although at optimum anti-microbial concentrations, Magainins are not cytotoxic, however, at higher concentrations Magainins exhibit cytotoxic activity. This activity is considered a significant attribute of the Magainin peptides in that it permits their use in the killing of animal cells. The activity of these peptides has been tested against a panel of a variety of cells listed in Table VI. As seen, Magainin II(g) immediately permeates a broad spectrum of cell type. The most resistant appears to be the epithelial cell from the oral mucosa. The most sensitive is a transformed monkey kidney cell. These results indicate the utility of Magainins as therapeutic cytotoxic agents. This includes anti-tumor activity, in vivo cytolysis or growth inhibition of malignant cells, such as in leukemias and selective reduction in specific cell populations (e.g., removal of lymphocytes from blood).

Cells were suspended in standard minimal Eagles medium containing 10% fetal calf serum. VERO cells and KB cells were obtained from the American Type Culture Collection. Human diploid fibroblasts were propagated from a primary dermal biopsy. Human lymphocytes were collected from a buffy coat preparation by centrifugation in ficoll-hyapaque medium. Human buccal epithelium was obtained by scraping the oral mucosa with a glass cover-slip and resuspending the cellular scraping in MEM. Cytotoxicity was determined by loss of Trypan Blue exclusion, following addition of dye to the medium. Cytotoxicity was assessed 30 minutes after addition of the peptide. Concentration noted represents the concentration of peptide resulting in 50% toxicity as determined visually by light microscopic examination of the treated cells.

TABLE VI

Cytotoxic Activity of Magainin(g)

| Cell | Concentration (μg/ml) |
|---|---|
| Vero Cells | 25 |
| Peripheral Human Lymphocytes | 75 |
| Human KB Cells | 125 |
| Human Diploid Fibroblasts | 250 |
| Human Buccal Epithelial Cells | 500 |

Spermicidal Activity of Magainin Peptides

The activity of Magainin II(g) was determined against human sperm since the peptides were shown to exhibit cytotoxic activity against a variety of human cells. Magainin II(g) was added in various concentrations to a suspension of human sperm in phosphate buffered saline. Motility was assayed by visual inspection under a light microscope. Observations were conducted at room temperature (about 22°–25° C.). The approximate number of motile sperm observed in 20 independent fields was noted as a function of concentration. Magainin II(g) inhibits sperm motility by 50% at 35 μg/ml and by 100% at 75 μg/ml. These results indicate that Magainin II(g) and other derivatives are useful as spermicide and hence, as contraceptive agent. The association of anti-microbial activity of the Magainin peptides along with its spermicidal activity indicates that this family of peptides represents ideal spermicidal agents.

Anti-Viral Activity of Magainin Peptides

The anti-vital activity of Magainin was tested against the presumptive AIDS virus, HTLV III in vitro and has been found in three repeated studies to exhibit anti-viral activity. HTLV III was obtained from culture media from the producing cell line A.3101. The media was diluted with MEM containing 10% fetal calf serum (FCS) to a viral concentration of about $10^4$ pfu/ml. Magainin II(g) was added to the viral innoculum (1 ml) to a concentration of 200 μg/ml and incubated at 37° C. for 30 min. The viral innoculum was then added to a well containing $10^3$ tester cells (cell line, SUPT1) and 1 ml of MEM with 10% FCS. Viral activity was assessed by formation of syncytia and cell death in the test cell culture as compared with cell cultures unexposed to Magainin peptides. After an incubation period of 2 weeks Magainin-exposed cultures appeared identical to cultures not exposed to virus, while untreated cultures were fully destroyed. Assay of reverse transcriptase activity in the culture fluids of untreated and treated wells revealed that Magainin treated samples exhibited no greater reverse transcriptase activity than uninfected cells, corroborating the visual assessment of cellular protection.

These studies demonstrate that the Magainin peptides have the potential to reduce the infectivity of the AIDS virus, HTLV III. The use of the Magainin peptides as a sterilant against this virus or as a chemotherapeutic agent for treating AIDS is thus indicated.

The activity of the Magainin peptides against HTLV III in vitro suggests that these peptides will exhibit anti-viral activity against other viral agents. The property of the Magainin peptides to disrupt certain membrane structures leads to the obvious application of these peptides against other membrane enclosed viruses, of which HTLV III is only a representative organism. Other candidates include herpes viruses, hepatitis B virus, retroviruses such as feline leukemia virus and HTLV I, and influenza virus.

Of course, pharmaceutical compositions comprising Magainin polypeptides of the present invention as an active ingredient in an amount sufficient to produce antibiotic effect in susceptible host or tissue and a pharmaceutically acceptable, non-toxic sterile carrier can be easily prepared based on the data provided herein. Such carriers could be fillers, non-toxic buffers, physiological saline solution and the like. The preparation can be used topically or systemically and may be in any suitable form such as liquid, solid or semi-solid, which include injectable solutions, tablets, ointments, lotions, pastes, capsules and the like. Of course, the Magainins may also be administered in combination with other adjuvants, protease inhibitors, or compatible drugs where such combination is seen desirable or advantageous in controlling the infection caused by harmful microorganisms including protozoa, viruses and the like.

It is understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A peptide selected from the group consisting of amide- and carboxy-terminated peptides having the following amino acid sequences:

(a) GIGKFLHSAGKFGKAFVGEIMKS;
    (b) GIGKFLHSAKKFGKAFVGEIMNS;
    (c) GIGKFLHSAKKFGKAFVGEIMN;
    (d) IGKFLHSAKKFGKAFVGEIMNS;
    (e) GKFLHSAKKFGKAFVGEIMNS;
    (f) KFLHSAKKFGKAFVGEIMNS;
    (g) FLHSAKKFGKAFVGEIMNS; and
    (h) LHSAKKFGKAFVGEIMNS.

2. The peptide of claim 1 wherein said peptide has the amino acid sequence:

GIGKFLHSAGKFGKAFVGEIMKS.

3. The peptide of claim 1 wherein said peptide has the amino acid sequence:

GIGKFLHSAKKFGKAFVGEIMNS.

4. The peptide of claim 1 wherein said peptide has the amino acid sequence:

GIGKFLHSAKKFGKAFVGEIMN.

5. The peptide of claim 1 wherein said peptide has the amino acid sequence:

IGKFLHSAKKFGKAFVGEIMNS.

6. The peptide of claim 1 wherein said peptide has the amino acid sequence:

GKFLHSAKKFGKAFVGEIMNS.

7. The peptide of claim 1 wherein said peptide has the amino acid sequence:

KFLHSAKKFGKAFVGEIMNS.

8. The peptide of claim 1 wherein said peptide has the amino acid sequence:

FLHSAKKFGKAFVGEIMNS.

9. The peptide of claim 1 wherein said peptide has the amino acid sequence:

LHSAKKFGKAFVGEIMNS.

10. A composition, comprising:
  (a) a peptide selected from the group consisting of:

$(NH_2)$ GIGKFLHSAGKFGKAFVGEIMKS $(OH)$, $(NH_2)$ GIGKFLHSAKKFGKAFVGEIMNS $(OH)$, $(NH_2)$ GIGKFLHSAKKFGKAFVGEIMN $(OH)$, $(NH_2)$ IGKFLHSAKKFGKAFVGEIMNS $(OH)$, $(NH_2)$ GKFLHSAKKFGKAFVGEIMNS $(OH)$, $(NH_2)$ KFLHSAKKFGKAFVGEIMNS $(OH)$, $(NH_2)$ FLHSAKKFGKAFVGEIMNS $(OH)$, and $(NH_2)$ LHSAKKFGKAFVGEIMNS $(OH)$, or their carboxy-terminal amides; and (b) a pharmaceutically acceptable carrier.

11. The composition of claim 10 wherein the peptide has the following structural formula:

$(NH_2)$ GIGKFLHSAGKFGKAFVGEIMKS $(OH)$, or its carboxy-terminal amide.

12. The composition of claim 10 wherein the peptide has the following structural formula:

$(NH_2)$ GIGKFLHSAKKFGKAFVGEIMNS $(OH)$, or its carboxy-terminal amide.

13. The composition of claim 10 wherein the peptide has the following structural formula:

$(NH_2)$ GIGKFLHSAKKFGKAFVGEIMN $(OH)$ or its carboxy-terminal amide.

14. The composition of claim 10 wherein the peptide has the following structural formula:

$(NH_2)$ IGKFLHSAKKFGKAFVGEIMNS $(OH)$ or its carboxy-terminal amide.

15. The composition of claim 10 wherein the peptide has the following structural formula:

(NH$_2$) GKFLHSAKKFGKAFVGEIMNS (OH)

or its carboxy-terminal amide.

16. The composition of claim 10 wherein the peptide has the following structural formula:

(NH$_2$) KFLHSAKKFGKAFVGEIMNS (OH)

or its carboxy-terminal amide.

17. The composition of claim 10 wherein the peptide has the following structural formula:

(NH$_2$) FLHSAKKFGKAFVGEIMNS (OH)

or its carboxy-terminal amide.

18. The composition of claim 10 wherein the peptide has the following structural formula:

(NH$_2$) LHSAKKFGKAFVGEIMNS (OH)

or its carboxy-terminal amide.

* * * * *